United States Patent [19]

Sanfilippo et al.

[11] Patent Number: 5,137,890

[45] Date of Patent: Aug. 11, 1992

[54] 4-PHENYL TETRAHYDROPYRIDO(4,3-D)PYRIMIDINES

[75] Inventors: Pauline J. Sanfilippo, Flemington; Jeffery B. Press, Rocky Hill, both of N.J.

[73] Assignee: Ortho Pharmaceutical Corporation, Raritan, N.J.

[21] Appl. No.: 479,914

[22] Filed: Feb. 14, 1990

[51] Int. Cl.$^5$ .................. C07D 487/04; A61K 31/505
[52] U.S. Cl. ...................................... 514/258; 544/279
[58] Field of Search .......................... 544/279; 514/258

[56] References Cited

U.S. PATENT DOCUMENTS 4,500,525  2/1985  Winters et al. ...................... 514/210

FOREIGN PATENT DOCUMENTS 1033384  3/1963  United Kingdom .

OTHER PUBLICATIONS

CA 103: 6298v—potentially bioactive pyrimidine derivatives.
Deli, J.; Lorand, T.; Szabo, D.; Foldesi, A.
J. Med. Chem. 28 934 (1985).
Derwent Abstract 78-46841A/26.
Derwent Abstract 78-42059A/23.
Derwent Abstract 66-21740F/00.
Derwent Abstract 66-13509F/00.
Derwent Abstract 66-12353F/00.

*Primary Examiner*—John M. Ford
*Assistant Examiner*—Jyothsna Venkat
*Attorney, Agent, or Firm*—Benjamin F. Lambert

[57] ABSTRACT

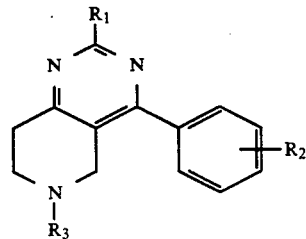

Novel tetrahydropyrido[4,3-d]pyrimidines and their synthesis are described. These compounds are useful for the treatment of gastrointestinal diseases, and are particularly useful as cytoprotective agents to prevent ulcer formation.

24 Claims, No Drawings

4-PHENYL TETRAHYDROPYRIDO(4,3-D)PYRIMIDINES

BACKGROUND OF THE INVENTION

1. Field of the Invention

The present invention relates to novel tetrahydropyrido[4,3-d]pyrimidines and their salts of the formula:

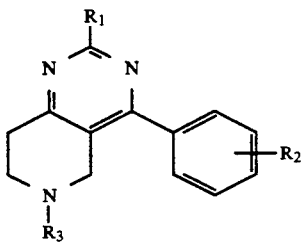

as described further below. These compounds are novel, and are useful in the treatment of gastrointestinal diseases, specifically as cytoprotective agents useful in the prevention of ulcer formation.

2. Description of the Prior Art

A 4-acetyl-2-(substituted benzoyl)piperidinone has been prepared by Gruppo Lepetit as described in *J. Med. Chem.* 28, 934 (1985) and in U.S. Pat. No. 4,500,525 (Feb. 19, 1985). This compound was used as an intermediate to prepare pyrazolo[4,3-c]pyridines which possess antihypertensive activity, as shown in the formula below.

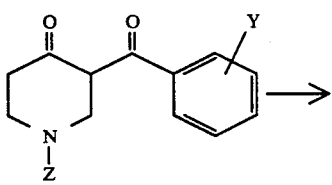

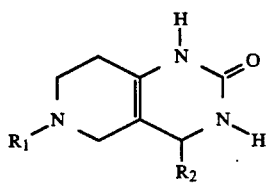

Derwent Publication Number 78-46841A/26 describes pyridopyrimidinones of the formula

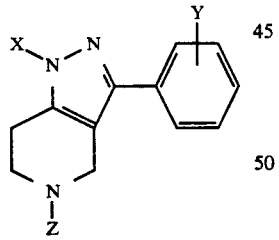

which have antidepressant and diuretic activity. In these compounds, $R_2$ may be an aryl group or a heterocycle.

Derwent Publication Number 78-42059A/23 describes 2-amino-8-arylidene-hexahydro-4-aryl-pryidopyrimidines of the formula

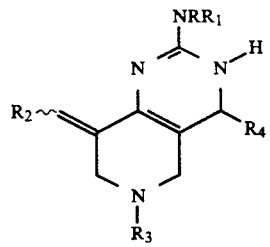

which are useful as central nervous system depressants, particularly muscle relaxants. In these compounds, $R_4$ may be an aryl group, pyridyl group or thienyl group.

Derwent Publication Numbers 66-21740F/00, 66-13509F/00 and 66-12353F/00 describe tetrahydropyrido[4,3-d]hydroxypyrimidines of the formula

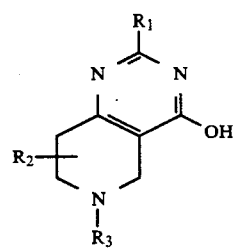

which are useful as antiphlogistics, diuretics, antipyretics, sedatives and coronary vasodilators.

SUMMARY OF THE INVENTION

The present invention is directed to tetrahydropyrido[4,3-d]pyrimidine compounds and their salts of the formula

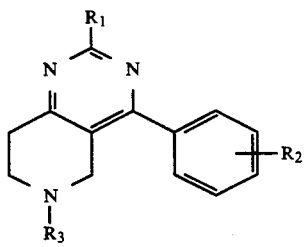

where $R_1$ may be $C_1$–$C_3$ alkyl, thiol, alkylthio, amino or substituted amino, wherein said substituted amino may be substituted either singularly or in combination with $C_1$–$C_3$ alkyl, $C_2$–$C_4$ acyl, phenyl or substituted phenyl, $R_2$ may be hydrogen, halogen, $C_1$–$C_4$ alkyl, $C_1$–$C_4$ alkoxy, trifluoromethyl, amino or substituted amino, wherein said substituted amino may be substituted either singularly or in combination with $C_1$–$C_3$ alkyl, $C_2$–$C_4$ acyl, phenyl or substituted phenyl, wherein said substituted phenyl may be substituted with halogen, $C_1$–$C_4$ alkyl, $C_1$–$C_4$ alkoxy or $C_2$–$C_4$ acyl; and $R_3$ may be hydrogen, $C_2$–$C_4$ acyl, benzoyl, substituted benzoyl, $C_1$–$C_4$ alkyl, substituted $C_1$–$C_4$ alkyl or allyl, wherein said substituted benzoyl may be substituted with halogen, $C_1$–$C_4$ alkyl, $C_1$–$C_4$ alkoxy or $C_2$–$C_4$ acyl, and said substituted alkyl may be substituted either singularly or in combination with halogen, phenyl, substituted phenyl, amino or substituted amino, wherein said substituted phenyl may be substituted with halogen, $C_1$–$C_4$ alkyl, $C_1$–$C_4$ alkoxy or $C_2$–$C_4$ acyl, and said substituted amino may be substituted either singularly or in combination with $C_1$–$C_3$ alkyl, $C_1$–$C_5$ cycloalkyl, phenyl or substituted phenyl, wherein said substituted phenyl may be substituted with halogen, $C_1$–$C_4$ alkyl, $C_1$–$C_4$ alkoxy or $C_2$–$C_4$ acyl.

The compounds of this invention are useful for the treatment of gastrointestinal diseases in mammals, and are specifically useful as cytoprotective agents for the prevention of ulcer formation.

DETAILED DESCRIPTION OF THE INVENTION

The invention in its broadest aspects relates to tetrahydropyrido[4,3-d]pyrimidine compounds which have utility in the treatment of gastrointestinal diseases, and specifically as cytoprotective agents useful in the prevention of ulcer formation. The compounds of the invention demonstrating an antisecretory activity are shown by the formula above. The preferred compounds of the present invention are those in which $R_1$ is $C_1$–$C_3$ alkyl, thiol, amino or substituted amino;
$R_2$ is hydrogen or halogen; and
$R_3$ is hydrogen, $C_2$–$C_4$ acyl, $C_1$–$C_4$ alkyl or substituted $C_1$–$C_4$ alkyl.

The compounds of the invention can be prepared as shown in the scheme below.

SCHEME

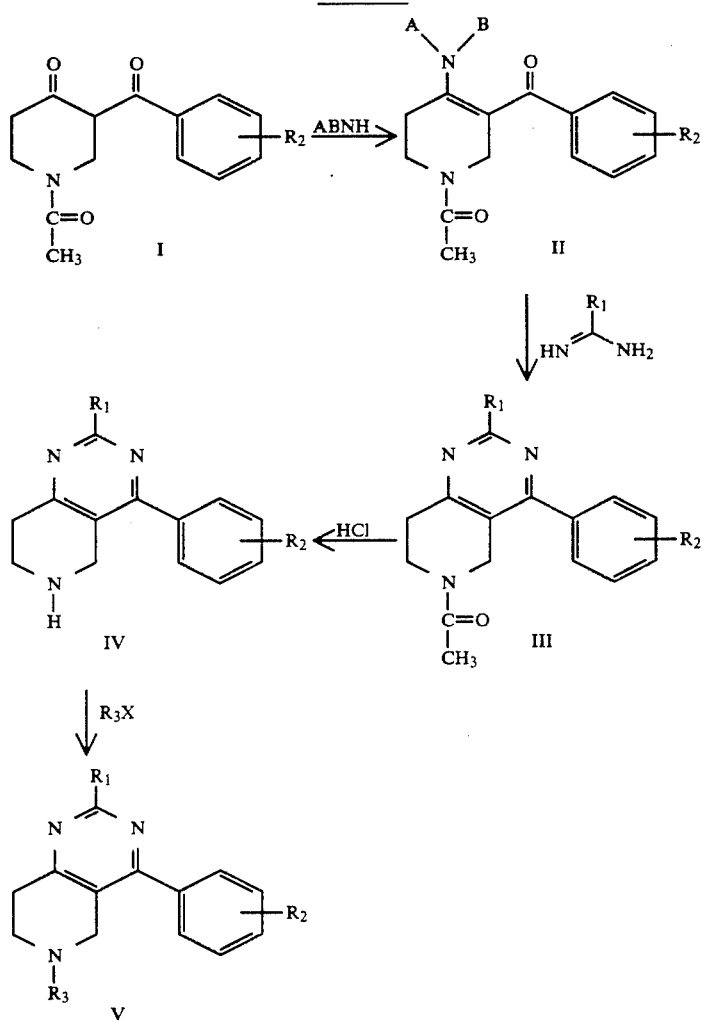

A 4-acetyl-2(substituted benzoyl)piperidone (I) is treated with an amine such as morpholine, pyrrolidine, piperidine or diethylamine in a suitable solvent such as benzene, toluene, xylenes, dichlorobenzene or methylene chloride at about 25° to 150° C. for a period of about 3 to 60 hours. The resulting enaminoketone (II) is treated with a substituted amidine, substituted guanidine or thiourea in the presence of a base such as sodium ethoxide, sodium methoxide, sodium hydride, potassium carbonate or triethylamine in a suitable solvent such as ethanol, methanol, propanol, dimethylformamide, dimethylsulfoxide or tetrahydrofuran at about 25° to 150° C. for 1 to 24 hours. The resulting acetylated pyrido[4,3-d]pyrimidine (III) is then treated with an aqueous acid such as hydrochloric acid, sulfuric acid, nitric acid or p-toluenesulfonic acid, or an aqueous base such as sodium hydroxide, potassium hydroxide, potassium carbonate or sodium carbonate.

The resulting secondary amine (IV) is treated with an alkylating agent such as iodomethane, iodoethane, iodopropane, iodobutane, allyl bromide, benzyl bromide or a substituted benzyl bromide in the presence of a base such as triethylamine, potassium carbonate, sodium hydride, sodium methoxide or sodium hydroxide in a suitable solvent such as methylene chloride, ethyl ether, tetrahydrofuran, dimethylformamide, dimethylsulfoxide or benzene at 10° to 100° C. to yield the tetrahydropyrido[4,3-d]pyrimidine[V].

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain a dosage per unit, e.g., tablet, capsule, powder, injection, teaspoonful and the like, from about 0.5 to about 100 mg/kg, and preferably from about 1 to about 5 mg/kg of the active ingredient.

The following examples describe the invention in greater particularity and are intended to illustrate but not limit the invention.

EXAMPLE 1

6-Acetyl-4-(4-chlorophenyl)-2-methyl-5,6,7,8-tetrahydropyrido[4,3-d]pyrimidine

A solution of 4-acetyl-2-(4-chlorobenzoyl)piperidinone (30.7 g, 100 mmol) and morpholine (10 mL, 100 mmol) in benzene (400 mL) was heated at reflux under Dean-Stark conditions for 5 hours. The solution was cooled to room temperature at which time it solidified. The resulting precipitate was collected by filtration, washed once with ethyl ether and dried in vacuo to give 20.3 g (58%) of a chloro-substituted morpholine-enamine ketone as yellow solid.

To a solution of sodium hydride (1.3 g, 56.5 mmol) in ethanol (200 mL) was added the morpholine-enamine ketone (10 g, 28.7 mmol) and acetamidine hydrochloride (5.4 g, 57 mmol). The mixture was heated to reflux for 3 hours, then cooled to room temperature overnight. The resulting precipitate was collected by filtration, washed with water and dried in vacuo to give 6.5 g (76%) of 6-acetyl-4-(4-chlorophenyl)-2-methyl-5,6,7,8-tetrahydropyrido[4,3-d]pyrimidine as a white solid, m.p. 139°-141° C. MS: 302(MH+).

Theor. $C_{16}H_{16}ClN_3O$: C,63.68; H,5.35; N,13.92.
Found: C,63.61; H,5.42; N,13.88.

EXAMPLE 2

6-Acetyl-4-(4-fluorophenyl)-2-methyl-5,6,-7,8-tetrahydropyrido[4,3-d]pyrimidine Monohydrochloride Monohydrate A solution of 4-acetyl-2-(4-fluorobenzoyl)piperidinone (77.8 g, 290 mmol) and morpholine (28 mL, 330 mmol) in benzene (600 mL) was heated at reflux under Dean-Stark conditions for 5 hours. The solution was cooled to room temperature at which time it solidified. The resulting precipitate was collected by filtration recrystallized from methylene chloride-ethyl ether and dried in vacuo to give 42.3 g (44%) of a fluoro-substituted morpholine-enamine ketone as a yellow solid.

To a solution of sodium hydride (1.4 g, 60.9 mmol) in ethanol (200 mL) was added the morpholine-enamine ketone (10 g, 30.1 mmol) and acetamidine hydrochloride (5.4 g, 57 mmol). The mixture was heated to reflux for 3 hours, then cooled to room temperature overnight. The resulting precipitate was collected by filtration, washed with water and dried in vacuo. The hydrochloride salt was prepared by adding concentrated hydrochloric acid to a solution of the free base in methanol and recrystallized from acetone to give 2.6 g (25%) of 6-acetyl-4-(4-fluorophenyl)-2-methyl-5,6,7,8-tetrahydropyrido[4,3-d]pyrimidine monohydrochloride monohydrate as a white solid. m.p. 116°-118° C. MS: 286 (MH+).

Theor. $C_{16}H_{16}FN_3O \cdot HCl \cdot H_2O$: C, 56.55; H,5.64; N,12.36.
Found: C,56.56; H,5.63; N,12.28.

EXAMPLE 3

6-Acetyl-4-(4-chlorophenyl)-5,6,7,8-tetrahydro-2-thiopyrido[4,3-d]pyrimidine Monohydrate The title compound was prepared as described in Example 1 starting with morpoline enamino-ketone (5.0 g, 14.3 mmol) and thiourea (2.2 g, 29.0 mmol) to give 1.2 g (26%) of 6-Acetyl-4-(4-chlorophenyl)-5,6,7,8-tetrahydro-2-thiopyrido[4,3-d]pyrimidine monohydrate.
m.p. 194°-196° C. MS: 320 (MH+).

Theor. $C_{15}H_{14}ClN_3OS \cdot H_2O$: C,55.33; H,4.77; N,12.44.
Found: C,53.99; H,4.35; N,12.59.

EXAMPLE 4

4-(4-Chlorophenyl)-2-(4-trifluoromethylphenylamino)-5,6,7,8-tetrahydropyrido[4,3-d]pyrimidine Monohydrochloride A mixture of 6-acetyl-4-(4-chlorophenyl)-2-(4-trifluoromethylphenylamino)-5,6,7,8-tetrahydropyrido[4,3-d]pyrimidine monohydrochloride (1.6 g, 3.3 mmol) in 40 mL of aqueous 10% hydrochloric acid was heated to reflux for 60 hours. The mixture was cooled to room temperature and the resulting solid was collected by filtration and recrystallized from water to give 1.1 g (75%) of 4-(4-chlorophenyl)-2-(4-trifluoromethylphenylamino)-5,6,7,8-tetrahydropyrido[4,3-d]pyrimidine monohydrochloride. m.p.>250° C. MS: 405 (MH+).

Theor. $C_{20}H_{16}ClF_3N_4 \cdot HCl$: C,54.43: H,3.88; N,12.70.
Found: C,54.38; H,3.89; N,12.58.

EXAMPLE 5

4-(4-Chlorophenyl)-6-ethyl-2-(4-trifluromethylphenylamino) -5,6,7,8-tetrahydropyrido[4,3-d] pyrimidine Dihydrochloride Monohydrate A mixture of 4-(4-chlorophenyl)-2-(4-trifluoromethylphenylamino) -5,6,7,8-tetrahydropyrido[4,3-d]pyrimidine monohydrochloride (0.70 g, 1.73 mmol), triethylamine (0.5 mL, 3.6 mmol) and iodoethane (0.14 mL, 1.73 mmol) in ethanol (20 mL) was heated to reflux overnight. The mixture was cooled to room temperature, concentrated in vacuo, and chromatographed (silica gel, 5% methanol in methylene chloride). The hydrochloride salt was prepared by adding concentrated hydrochloric acid to a solution of the free base in methanol and recrystallized from acetone to give 0.21 g (28%) of 4-(4-chlorophenyl)-6-ethyl-2-(4-trifluromethylphenylamino)-5,6,7,8-tetrahydropyrido[4,3-d]pyrimidine dihydrochloride monohydrate. m.p. 273°-275° C. MS: 433 (MH+).

Theor. $C_{22}H_{20}ClF_3N_4.2HCl.H_2O$: C,50.45: H,4.62: N,10.70.
Found: C,50.47: H,4.51: N,10.66.

EXAMPLE 6

6-Acetyl-4-(4-chlorophenyl)-2-ethylamino-5,6,7,8-tetrahydropyrido[4,3-d]pyrimidine The title compound was prepared as described in Example 1 starting with the morpholine-enamine ketone (8.2 g, 23.5 mmol) and using ethylguanidine hydrochloride (5.8 g, 47.0 mmol) in place of acetamidine hydrochloride to produce 3.3 g (42%) of 6-acetyl-4-(4-chlorophenyl)-2-ethylamino-5,6,7,8-tetrahydropyrido[4,3-d]pyrimidine. m.p. 150°-152° C. MS: 331 (MH+).

Theor. $C_{17}H_{19}ClN_4O$: C,61.72; H,5.79; N,16.94.
Found: C,61.62; H,5.86; N,16.59.

EXAMPLE 7

6-Acetyl-4-(4-fluorophenyl)-2-ethylamino-5,6,7,8-tetrahydropyrido[4,3-d]pyrimidine The title compound was prepared as described in Example 2 starting with the morpholine-enamine ketone (11.2 g, 32.2 mmol) and using ethylguanidine hydrochloride (8.3 g, 33.7 mmol) in place of acetamidine hydrochloride to produce 9.2 g (86%) of 6-acetyl-4-(4-fluorophenyl)-2-ethylamino-5,6,7,8-tetrahydropyrido[4,3-d]pyrimidine. m.p. 136°-138° C. MS: 315 (MH+).

Theor. $C_{17}H_{19}FN_4O$: C,64.95; H,6.09; N,17.82.
Found: C,64.80; H,6.18; N,17.62.

EXAMPLE 8

4-(4-Chlorophenyl)-2-ethylamino-5,6,7,8-tetrahydropyrido[4,3-d]pyrimidine Hemihydrate The title compound was prepared as described in Example 4 starting with 6-acetyl-4-(4-chlorophenyl)-2-ethylamino-5,6,7,8-tetrahydropyrido[4,3-d]pyrimidine (2.5 g, 7.6 mmol) to produce 0.86 g (38%) of 4-(4- chlorophenyl)-2-ethylamino-5,6,7,8-tetrahydropyrido[4,3-d]pyrimidine hemihydrate. m.p. 155°-157° C. MS: 289 (MH+).

Theor. $C_{15}H_{17}ClN_4.\frac{1}{2}H_2O$: C,60.50; H,6.09; N,18.81.
Found: C,60.59; H,6.07; N,18.56.

EXAMPLE 9

6-Allyl-4-(4-chlorophenyl)-2-ethylamino-5,6,7,8-tetrahydropyrido[4,3-d]pyrimidine A suspension of sodium hydride (0.74 g, 18.5 mmol), washed three times pentanes, in dimethylformamide (40 mL) was treated with 4-(4-chlorophenyl)-2-ethylamino-5,6,7,8-tetrahydropyrido[4,3-d]pyrimidine hydrochloride (3.0 g, 9.3 mmol). The mixture was stirred at room temperature for 2 hours and allylbromide (0.8 mL, 9.3 mmol) was added. This mixture was then stirred at room temperature overnight, quenched with water and the resulting oil was chromatographed (silica gel; acetone) to give 2.7 g (89%) of 6-allyl-4-(4-chlorophenyl)-2- ethylamino-5,6,7,8-tetrahydropyrido[4,3-d]pyrimidine. m.p. 104°-106° C. MS: 329 (MH+).

Theor. $C_{18}H_{21}ClN_4$: C,65.74; H,6.44; N,17.04.
Found: C,65.83; H,6.39; N,16.86.

EXAMPLE 10

6-Benzyl-4-(4-chlorophenyl)-2-ethylamino-5,6,7,8-tetrahydropyrido[4,3-d]pyrimidine The title compound was prepared as described in Example 5 starting with 4-(4-chlorophenyl)-2-ethylamino- 5,6,7,8-tetrahydropyrido[4,3-d]pyrimidine hydrochloride (1.1 g, 3.4 mmol) and benzyl bromide (0.4 mL, 3.4 mmol) to produce 0.35 g (27%) of 6-benzyl-4-(4- chlorophenyl)-2-ethylamino-5,6,7,8-tetrahydropyrido[4,3-d]pyrimidine. m.p. 138°-141° C. MS: 379 (MH+).

Theor. $C_{22}H_{23}ClN_4$: C,69.74; H,6.12; N,14.79.
Found: C,69.33; H,6.22; N,14.59.

EXAMPLE 11

4-(4-Chlorophenyl)-6-ethyl-2-ethylamino-5,6,7,8-tetrahydropyrido[4,3-d]pyrimidine The title compound was prepared as described in Example 9 starting with 4-(4-chlorophenyl)-2-ethylamino-5,6,7,8-tetrahydropyrido[4,3-d]pyrimidine hydrochloride (3.0 g, 9.3 mmol) and iodoethane (0.74 mL, 18.5 mmol) to produce 2.9 g (100%) of 4-(4-chlorophenyl)-6-ethyl-2- ethylamino-5,6,7,8-tetrahydropyrido[4,3-d]pyrimidine. m.p. 129°-132° C. MS: 317 (MH+).

Theor. $C_{17}H_{21}ClN_4$: C,64.45; H,6.68; N,17.68.
Found: C,63.90; H,6.69; N,17.47.

EXAMPLE 12

2-Ethylamino-4-(4-fluorophenyl)5,6,7,8-tetrahydropyrido[4,3-d]pyrimidine Monohydrochloride The title compound was prepared as described in Example 4 starting with 6-acetyl-4-(4-fluorophenyl)-2-ethylamino-5,6,7,8-tetrahydropyrido[4,3-d]pyrimidine (5.7 g, 18 mmol) to produce 5.6 g (100%) of 2-ethylamino-4-(4-fluorophenyl)-5,6,7,8-tetrahydropyrido[4,3-d]pyrimidine monohydrochloride. m.p.>230° C. MS: 273 (MH+).

Theor. $C_{15}H_{17}FN_4.HCl$: C,58.34; H,5.87; N,18.14.
Found: C,57.80; H,5.70; N,17.94.

EXAMPLE 13

6-Acetyl-2-amino-4-(4-chlorophenyl)-5,6,7,8-tetrahydropyrido[4,3-d]pyrimidine To a solution of 4-acetyl-2-(4-chlorobenzoyl)piperidinone (250 g, 896 mmol) in toluene (600 mL) was added pyrrolidine (80 mL, 960 mmol). The solution was stirred at room temperature overnight at which time the solution solidified. The resulting precipitate was collected by filtration, washed once with ethyl ether and dried in vacuo to give 119 g (40%) of pyrrolidine-enamine ketone as a yellow solid. m.p. 163°-165° C. MS: 333 (MH+).

To a solution of sodium hydride (17 g, 739 mmol) in ethanol (600 mL) was added the pyrrolidine-enamine ketone (119 g, 360 mmol) and guanidine hydrochloride (68 g, 720 mmol). The mixture was heated to reflux for 3 hours, then cooled to room temperature overnight. The resulting precipitate was collected by filtration, washed with water and dried in vacuo to give 99.7 g (82%) of 6-acetyl-2-amino-4-(4-chlorophenyl)-5,6,7,8-tetrahydropyrido[4,3-d]pyrimidine. m.p. 218°-220° C. MS: 303(MH+). IR(KBr): 3365, 3330, 3186, 1641, 1631 cm$^{-1}$.

$^1$H NMR (DMSO-d$_6$): ∂7.56 (m, 4H), 6.59 (s, 2H), 4.42 (s, 2H), 3.73 (t, J=2.1 Hz, 2H), 2.81 (t, J=2.1 Hz, 2H), 2.04 (s, 3H).

Theor. C$_{15}$H$_{15}$ClN$_4$O: C,59.51; H,4.99; N,18.50.
Found: C,59.24; H,5.11; N,18.37.

EXAMPLE 14

6-Acetyl-2-amino-4-(4-fluorophenyl)-5,6,7,8-tetrahydropyrido[4,3-d]pyrimidine Monohydrate The title compound was prepared as described in Example 13 starting with 4-acetyl-2-(4-fluorobenzoyl)-piperidinone (70.0 g 267 mmol) and guanidine hydrochloride (42.0 g, 438 mmol) to give 24.2 g (39%) of 6-acetyl-2-amino-4-(4-fluorophenyl)-5,6,7,8-tetrahydropyrido[4,3-d]pyrimidine monohydrate. m.p. 205°-207° C. MS: 287 (MH+).

$^1$H NMR (DMSO-d$_6$): ∂7.61 (m, 2H), 7.36 (m,2H), 6.56 (s,2H), 4.44 (s,2H), 3.74 (t, J=2.1 Hz, 2H), 2.81 (t, J=2.1 Hz, 2H), 2.04 (s,3H).

Theor. C$_{15}$H$_{15}$FN$_4$O.H$_2$O: C,59.20; H,5.63; N,18.41.
Found: C,58.94; H,5.55; N,18.32.

EXAMPLE 15

2-Amino-4-(4-chlorophenyl)-5,6,7,8-tetrahydropyrido[4,3-d]pyrimidine Dihydrochloride A mixture of 6-acetyl-2-amino-4-(4-chlorophenyl)-5,6,7,8-tetrahydropyrido[4,5-d]pyridine (5.0g, 16.5 mmol) in 60 mL of aqueous 10% hydrochloric acid was heated to reflux for 12 hours. The mixture was then cooled to room temperature and concentrated in vacuo. The resulting solid was triturated with methanol and collected by filtration to give 3.9 g (91%) of 2-amino-4-(4-chlorophenyl)-5,6,7,8-tetrahydropyrido[4,3-d]pyrimidine dihydrochloride. m.p. 283°-285° C. MS: 261 (MH+). IR(KBr): 3326, 2760, 2433, 1668 cm$^{-1}$.

$^1$H NMR(DMSO-d$_{26}$): ∂9.83(broad S, 2H), 7.63(m, 4H), 4.08(m, 2H), 3.41(m, 2H), 3.05 (t, J=2.1 Hz, 2H).

Theor. C$_{13}$H$_{13}$ClN$_4$.2HCl: C,46.79; H,4.53; N,16.79.
Found: C,46.36; H,4.79; N,16.62.

EXAMPLE 16

2-Amino-4-(4-fluorophenyl)-5,6,7,8-tetrahydropyridopyrido[4,3-d]pyrimidine Dihydrochloride Hemihydrate The title compound was prepared as described in Example 15 starting with 6-acetyl-2-amino-4-(4-fluorophenyl) -5,6,7,8-tetrahydropyrido[4,3-d]pyrimidine monohydrate (6.8 g, 24 mmol) to produce 5.9 g (75%) of 2-amino-4-(4-fluorophenyl)-5,6,7,8-tetrahydropyrido[4,3-d]pyrimidine dihydrochloride hemihydrate. m.p.>260° C. MS: 245 (MH+).

Theor. C$_{13}$H$_{13}$FN$_4$.2HCl.½H$_2$O: C,47.86; H,4.94; N,17.18.
Found: C,47.50; H,5.00; N,16.91.

EXAMPLE 17

2-Amino-4-(4-chlorophenyl)-6-ethyl-5,6,7,8-tetrahydropyrido[4,3-d]pyrimidine Dihydrochloride A suspension of sodium hydride (12.7 g, 320 mmol), washed three times pentanes, in dimethylformamide (200 mL) was treated with 2-amino-4-(4-chlorophenyl)-5,6,7,8-tetrahydropyrido[4,3-d]pyrimidine dihydrochloride (35.3 g, 110 mmol). The mixture was stirred at room temperature for 2 hours, and iodoethane (8.8 mL, 110 mmol) was added. The mixture was stirred at room temperature overnight, quenched with water and the resulting precipitate was collected by filtration to give 31.5 g (79%) of 2-amino-4-(4-chlorophenyl)-6-ethyl-5,6,7,8-tetrahydropyrido[4,3-d]pyrimidine dihydrochloride. m.p.>260° C. MS: 289 (MH+). IR(KBr): 3224, 2641, 2311, 1623 cm$^{-1}$.

$^1$H NMR (DMSO-d$_6$) ∂7.63 (m,6H), 4.32–4.11 (m,2H), 3.70–3.08 (m,6H), 1.25 (t,J=2.4 Hz,2H).

Theor. C$_{15}$H$_{17}$ClN$_4$.2HCl: C,49.80; H,5.29; N,15.49.
Found: C,49.57; H,5.33; N,15.38.

EXAMPLE 18

2-Amino-4-(4-fluorophenyl)-6-ethyl-5,6,7,8-tetrahydropyrido[4,3-d]pyrimidine

The title compound was prepared as described in Example 17 starting with 2-amino-4-(4-fluorophenyl)-5,6,7,8-tetrahydropyrido[4,3-d]pyrimidine dihydrochloride hemihydrate (1.8 g, 5.5 mmol) and iodoethane (0.4 mL, 5.5 mmol) to produce 0.91 g (48%) of 2-amino-4-(4-fluorophenyl)-6-ethyl-5,6,7,8-tetrahydropyrido[4,3-d]pyrimidine. m.p. 242°-243° C. MS: 273 (HM+). IR(KBr): 3301, 3132, 2575, 1626, 1604 cm$^{-1}$.

$^1$H NMR (DMSO-d$_6$) ∂7.63 (m,2H), 7.19 (m,2H), 4.39–3.01 (m,8H), 1.25 (t,J=2.4 Hz, 2H).

Theor. C$_{15}$H$_{17}$FN$_4$. 2HCl: C,52.18; H,5.55; N,16.28.
Found: C,52.02; H,5.33; N,16.16.

EXAMPLE 19

2-Amino-4-(4-chlorophenyl)-6-propyl-5,6,7,8-tetrahydropyrido[4,3-d]-pyrimidine Dihydrochloride ¼ Hydrate The title compound was prepared as described in Example 17 starting with 2-amino-4-(4-chlorophenyl)-5,6,7,8-tetrahydropyrido[4,3-d]pyrimidine dihydrochloride (4.0 g, 13.5 mmol) and iodopropane (1.3 mL, 13.5 mmol) instead of iodoethane to produce 2.1 g (51%) of 2-amino-4-(4-chlorophenyl)-6-propyl-5,6,7,8-tetrahydropyrido[4,3-d]pyrimidine dihydrochloride ¼ hydrate. m.p. 244°-246° C. MS: 303(HM+).

Theor. C$_{16}$H$_{19}$ClN$_4$.2HCl¼H$_2$O: C,50.53; H,5.70; N,14.73.
Found: C,50.32; H,5.67; N,14.71.

EXAMPLE 20

6-Allyl-2-amino-4-(4-chlorophenyl)-5,6,7,8-tetrahydropyrido[4,3-d]pyrimidine Dihydrochloride The title compound was prepared as described in Example 17 starting with 2-amino-4-(4-chlorophenyl)-5,6,7,8-tetrahydropyrido[4,3-d]pyrimidine dihydrochloride (1.5 g, 4.5 mmol) and allyl bromide (0.4 mL, 4.6 mmol) instead of iodoethane to produce 0.65 g (39%) of 6-allyl-2-amino-4-(4-chlorophenyl)-5,6,7,8-tetrahydropyrido[4,3-d]pyrimidine dihydrochloride. m.p. 248°–250° C. MS: 301 (MH+).

Theor. $C_{16}H_{17}ClN_4.2HCl$: C,51.42; H,5.12; N,14.99. Found: C,50.88; H,4.75; N,14.75.

EXAMPLE 21

6-Allyl-2-amino-4-(4-fluorophenyl)-5,6,7,8-tetrahydropyrido[4,3-d]pyrimidine Dihydrochloride The title compound was prepared as described in Example 17 starting with 2-amino-4-(4-fluorophenyl)-5,6,7,8-tetrahydropyrido[4,3-d]pyrimidine dihydrochloride hemihydrate (1.0 g, 3.1 mmol) and allyl bromide (0.3 mL, 3.1 mmol) instead of iodoethane to produce 0.65 g (59%) of 6-allyl-2-amino-4-(4-fluorophenyl)-5,6,7,8-tetrahydropyrido[4,3-d]pyrimidine dihydrochloride. m.p. 241°–243° C. MS: 285 (MH+). IR(KBr): 3305, 3118, 2476, 1651 cm$^{-1}$.

$^1$H NMR (DMSO-d$_6$) $\delta$7.64(m,2H), 7.41(m,2H), 6.00(m,1H), 5.45(m,2H), 4.19–3.01(m,8H).

Theor. $C_{16}H_{17}FN_4.2HCl$: C,53.79; H,5.36; N,15.68. Found: C,53.61; H,4.94; N,15.36.

EXAMPLE 22

2-Amino-4-(4-chlorophenyl)-6-methyl-5,6,7,8-tetrahydropyrido[4,3-d]pyrimidine ¼ Hydrate The title compound was prepared as described in Example 17 starting with 2-amino-4-(4-chlorophenyl)-5,6,7,8-tetrahydropyrido[4,3-d]pyrimidine dihydrochloride (5.0 g, 15.0 mmol) and iodomethane (0.9 mL, 15.0 mmol) instead of iodoethane to produce 0.42 g (11%) of 2-amino-4-(4-chlorophenyl)-6-methyl-5,6,7,8-tetrahydropyrido[4,3-d]pyrimidine ¼ hydrate. m.p. 172°–175° C. MS: 275 (MH+).

Theor. $C_{14}H_{15}ClN_4.\frac{1}{4}H_2O$: C,60.21; H,5.59; N,20.05. Found: C,60.03; H,5.45; N,20.36.

EXAMPLE 23

6-Acetyl-2-amino-4-phenyl-5,6,7,8-tetrahydropyrido[4,3-d]pyrimidine Monohydrate

The title compound was prepared as described in Example 13 starting with 4-acetyl-2-benzoylpiperidinone (15.0 g, 50.3 mmol) and guanidine hydrochloride (9.6 g, 100.6 mmol) to give 10.3 g (76%) of 6-acetyl-2-amino-4- phenyl-5,6,7,8-tetrahydropyrido[4,3-d]pyrimidine monohydrate. m.p.>270° C. MS: 269(MH+). $^1$H NMR (DMSO-d$_6$): $\delta$7.44–7.2(m, 5H), 6.56(s, 2H), 4.44(s, 2H), 3.74(t,J=2.1 Hz,2H), 2.81(t,J=2.1 Hz,2H), 2.04(s, 3H).

Theor $C_{15}H_{16}N_4O.H_2O$: C,62.92; H,6.33; N,19.57. Found: C,62.92; H,5.91; N,20.02.

EXAMPLE 24

6-Acetyl-2-methyl-4-(4-methylphenyl)-5,6,7,8-tetrahydropyrido[4,3-d]pyrimidine Monohydrate The title compound was prepared as described in Example 13 starting with 4-acetyl-2-(4-methylbenzoyl)-piperidinone (20.0 g, 64 mmol) and acetamidine hydrochloride (12.0 g, 128 mmol) to give 12.4 g (69%) of 6-acetyl-2-methyl-4-(4-methylphenyl)-5,6,7,8-tetrahydropyrido[4,3-d]pyrimidine monohydrate. m.p.>270° C. MS: 281(MH+).

$^1$H NMR (DMSO-d$_6$) $\delta$7.68(m, 2H), 7.46(m, 2H), 4.44(s, 2H); 3.74(t, J=2.1 Hz, 2H), 2.81(t, J=2.1 Hz, 2H), 2.11(s, 3H), 2.09(s, 3H), 2.04(s, 3H).

Theor. $C_{17}H_{19}N_3O.H_2O$: C,68.20; H,7.07; N,14.03. Found: C,68.47; H,7.28; N,14.19.

EXAMPLE 25

6-Acetyl-5,6,7,8-tetrahydro-4-(4-methylphenyl)-2-dipropylaminopyrido[4,3-d]-pyrimidine Monohydrate The title compound was prepared as described in Example 17 starting with 6-acetyl-2-amino-4-(4-methylphenyl)-5,6,7,8-tetrahydropyrido[4,3-d]pyrimidine (2.0 g, 8.3 mmol) and iodopropane (1.4 mL, 14.5 mmol) to give 1.2 g (40%)of6-acetyl-5,6,7,8-tetrahydro-4-(4-methylphenyl)-2-dipropylaminopyrido[4,3-d]pyrimidinemonohydrate. m.p. >270° C. MS: 367(MH+).

$^1$H NMR (DMSO-d$_6$) $\delta$7.61(m, 2H), 7.36(m, 2H), 4.44(s, 2H), 4.35(m, 4H), 3.74(t, J=2.1 Hz, 2H), 2.81(t, J=2.1 Hz, 2H), 2.04(s, 3H), 1.98(m, 4H), 1.11(m, 6H).

Theor. $C_{22}H_{33}N_4O.HCl.H_2O$: C,62.77; H,7.90; N,13.31. Found: C,62.73; H,7.50; N,13.67.

EXAMPLE 26

2-Amino-6-(2-diethylaminoethyl)-4-(4-fluorophenyl)-5,6,7,8-tetrahydropyrido[4,3-d]pyrimidine Trihydrochloride The title compound was prepared as described in Example 17 starting with 2-amino-4-(4-fluorophenyl)-5,6,7,8-tetrahydropyrido[4,3-d]pyrimidine (2.0 g, 8.2 mmol) and diethylaminoethylchloride hydrochloride (2.8 g, 16.4 mmol) to give 1.1 g (39%) of 2-amino-5-(2-diethylaminoethyl)-4-(4-fluorophenyl)-5,6,7,8-tetrahydropyrido[4,3-d]pyrimidine trihydrochloride. m.p. 234°–236° C. MS: 343(MH+).

$^1$H NMR (DMSO-d$_6$): $\delta$7.61(m, 2H), 7.42(m, 2H), 4.44(s, 2H), 4.34(m, 4H), 4.21(m, 4H), 3.74(t, J=2.1 Hz, 2H), 2.81(t, J=2.1 Hz, 2H), 2.10(m, 2H), 1.21(m, 6H).

Theor. $C_{19}H_{26}N_5F.3HCl$: C,50.39; H,6.45; N,15.47. Found: C,49.95; H,6.66; N,15.40.

EXAMPLE 27

2-Amino-4-(4-fluorophenyl)-5,6,7,8-tetrahydro-5-(3-dimethylaminopropyl) pyrido[4,3-d]pyrimidine Trihydrochloride The title compound was prepared as described in Example 17 starting with 2-amino-4-(4-fluorophenyl)-5,6,7,8-tetrahydropyrido[4,3-d]pyrimidine (2.0 g, 8.2 mmol) and dimethylaminopropylchloride hydrochloride (2.6 g, 16.4 mmol) to give 0.91 g (34%) of 2-amino-4-(4-fluorophenyl)-5,6,7,8-tetrahydro-5-(3-dimethylaminopropyl)pyrido[4,3-d]pyrimidine trihydrochloride. m.p. 241°–243° C. MS: 329(MH+).

$^1$H NMR (DMSO-d$_6$) $\delta$7.61(m, 2H), 7.42(m, 2H), 4.44(s, 2H), 4.34(m, 4H), 4.21(m, 4H), 4.11(s, 6H), 3.74(t, J=2.1 Hz, 2H), 2.81(t, J=2.1 Hz, 2H), 2.10(m, 2H).

Theor. $C_{18}H_{24}N_5F.3HCl$: C,49.27; H,6.20; N,15.96. Found C,48.87; H,6.21; N,15.86.

EXAMPLE 28

Biological Activity (Cytoprotection)

Using the procedures of Robert, A. et al., *Gastroenterology* 77, 433(1979), male, Charles River rats weighing between 140 and 220 g were fasted overnight, but allowed water ad libitum. The rats were, however, deprived of water during the experiment.

The rats were weighed and pretreated orally with the example compounds at the doses shown below in Table 1. One hour later, the necrotizing agent, 50% ethanol, was administered orally in a dose volume of 1 ml/animal. After an additional hour, the rats were sacrificed with $CO_2$, the stomachs removed, inflated with distilled water, opened along the greater curvature and laid out on a flat surface.

The presence of mucosal bleeding was noted and after wiping off the mucosa, the presence of submucosal bleeding was also noted. The incidence of lesions in the mucosa and the submucosa was statistically analyzed by the method of Chisquares using Yates correction.

The results of the experiments are presented below in Table 1.

TABLE 1

| Compounds of Example | Inhibition of Ethanol-Induced Lesions (mg/kg) |
|---|---|
| 1 | 20% @ 10 |
| 2 | 100% @ 10[a] |
| 3 | |
| 4 | |
| 5 | 20% @ 10 |
| 6 | |
| 7 | $ED_{50}$ = 5.0(3.0–7.8) |
| 8 | |
| 9 | 80% @ 10 |
| 10 | 20% @ 10 |
| 11 | $ED_{50}$ = 9.5(2.0–17.6) |
| 12 | $ED_{50}$ = 4.7(2.2–7.4)[b] |
| 13 | $ED_{50}$ ≈ 3 |
| 14 | 80% @ 10 |
| 15 | 40% @ 10 |
| 16 | 80% @ 10 |
| 17 | $ED_{50}$ = 3.2(1.3–23.3)[c] |
| 18 | $ED_{50}$ = 3.7(0.6–6.5)[e] |
| 19 | $ED_{50}$ = 2.7(1.6–5.4) |
| 20 | $ED_{50}$ = 7.9(4.6–14.0) |
| 21 | $ED_{50}$ = 5.0(2.0–12.8) |
| 22 | 100% @ 10 |
| 23 | $ED_{50}$ = 2.3(2.2–7.4)[d] |
| 24 | 40% @ 10 |
| 25 | 40% @ 10 |
| 26 | 80% @ 10 |
| 27 | $ED_{50}$ ≈ 7.0 |

[a] 8/10 at 20 mg/kg vs. 80 mg/kg aspirin
[b] 8/10 at 10 mg/kg vs. 80 mg/kg aspirin
[c] $ED_{50}$ = 14.5(2.2–7.4) mg/kg vs. 80 mg/kg aspirin
[d] $ED_{50}$ = 9.5(4.0–18.4) mg/kg vs. 80 mg/kg aspirin
[e] 8/10 at 40 mg/kg v. 80 mg/kg aspirin

What is claimed is:

1. A compound of the formula

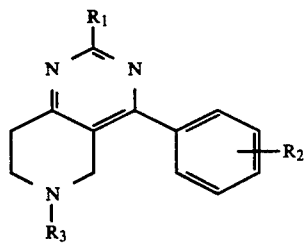

where
$R_1$ is $C_1$–$C_3$ alkyl, thiol, alkylthio, amino or substituted amino,
wherein said substituted amino is substituted either singularly or in combination with $C_1$–$C_3$ alkyl, $C_2$–$C_4$ acyl, phenyl or substituted phenyl,
wherein said substituted phenyl is substituted with halogen, $C_1$–$C_4$ alkyl, $C_2$–$C_4$ acyl or trifluoromethyl;
$R_2$ is hydrogen, halogen, $C_1$–$C_4$ alkyl, $C_1$–$C_4$ alkoxy, trifluoromethyl, amino or substituted amino,
wherein said substituted amino is substituted either singularly or in combination with $C_1$–$C_3$ alkyl, $C_2$–$C_4$ acyl, phenyl or substituted phenyl,
wherein said substituted phenyl is substituted with halogen, $C_1$–$C_4$ alkyl, $C_1$–$C_4$ alkoxy or $C_2$–$C_4$ acyl; and
$R_3$ is hydrogen, $C_2$–$C_4$ acyl, benzoyl, substituted benzoyl, $C_1$–$C_4$ alkyl, substituted $C_1$–$C_4$ alkyl or allyl,
wherein said substituted benzoyl is substituted with halogen, $C_1$–$C_4$ alkyl, $C_1$–$C_4$ alkoxy or $C_2$–$C_4$ acyl, and said substituted alkyl is substituted either singularly or in combination with halogen, phenyl, substituted phenyl, amino or substituted amino,
wherein said substituted phenyl is substituted with halogen, $C_1$–$C_4$ alkyl, $C_1$–$C_4$ alkoxy or $C_2$–$C_4$ acyl, and said substituted amino is substituted either singularly or in combination with $C_1$–$C_3$ alkyl, $C_1$–$C_5$ cycloalkyl, phenyl or substituted phenyl,
wherein said substituted phenyl is substituted with halogen, $C_1$–$C_4$ alkyl, $C_1$–$C_4$ alkoxy or $C_2$–$C_4$ acyl and their salts.

2. The compound of claim 1 wherein
$R_1$ is $C_1$–$C_3$ alkyl, thiol, amino or substituted amino;
$R_2$ is hydrogen or halogen; and
$R_3$ is hydrogen, $C_2$–$C_4$ acyl, $C_1$–$C_4$ alkyl or substituted $C_1$–$C_4$ alkyl.

3. The compound of claim 1 selected from the group consisting of 6-acetyl-4-(4-chlorophenyl)-2-methyl-5,6,7,8-tetrahydropyrido[4,3-d]pyrimidine, 6-acetyl-4-(4-fluorophenyl)-2-methyl-5,6,7,8-tetrahydropyrido[4,3-d]pyrimidine monohydrochloride monohydrate and 6-acetyl-2-methyl-4-(4-methylphenyl)-5,6,7,8-tetrahydropyrido[4,3-d]pyrimidine monohydrate.

4. The compound of claim 1 wherein said compound is 6-acetyl-4-(4-chlorophenyl)-5,6,7,8-tetra-hydro-2thiopyrido[4,3-d]pyrimidine monohydrate.

5. The compound of claim 1 selected from the group consisting of 4-(4-chlorophenyl)-2-(4-trifluoromethylphenylamino) -5,6,7,8-tetrahydropyrido[4,3d]pyrimidine monohydrochloride and 4-(4-chlorophenyl) -6-ethyl-2-(4-trifluromethylphenylamino)-5,6,7,8-tetrahydropyrido[4,3-d]pyrimidine dihydrochloride monohydrate.

6. The compound of claim 1 selected from the group consisting of 6-acetyl-4-(4-chlorophenyl)-2-ethylamino -5,6,7,8-tetrahydropyrido[4,3-d]pyrimidine, 6- acetyl-4-(4-fluorophenyl)-2-ethylamino-5,6,7,8tetrahydropyrido[4,3-d]pyrimidine, 4-(4-chlorophenyl) -2-ethylamino-5,6,7,8-tetrahydropyrido[4,3-d]pyrimidine hemihydrate, 6-allyl-4-(4-chlorophenyl) -2-ethylamino-5,6,7,8-tetrahydropyrido[4,3d]pyrimidine, 4-4-chlorophenyl)-6-ethyl-2-ethylamino-5,6,7,8tetrahydropyrido[4,3-d]pyrimidine and2-ethylamino- 4-(4-fluorophenyl)-5,6,7,8-tetrahydropyrido[4,3-d]pyrimidine monohydrochloride.

7. The compound of claim 1 selected from the group consisting of 6-acetyl-2-amino-4-(4-chlorophenyl)-5,6,7,8-tetrahydropyrido[4,3-d]pyrimidine, 6-acetyl-2-amino-4-(4-fluorophenyl)-5,6,7,8-tetrahydropyrido[4,3-d]pyrimidine monohydrate, 2-amino-4-(4-chlorophenyl)-5,6,7,8-tetrahydropyrido[4,3-d]pyrimidine dihydrochloride, 2-amino-4-(4-fluorophenyl) -5,6,7,8-tetrahydropyrido[4,3-d]pyrimidine dihydrochloride hemihydrate, 2-amino-4-(4-chlorophenyl) -6-ethyl-5,6,7,8-tetrahydropyrido[4,3-d] pyrimidine dihydrochloride, 2-amino-4-(4-fluorophenyl) -6-ethyl-5,6,7,8-tetrahydropyrido[4,3-d]pyrimidine, 2-amino-4-(4-chlorophenyl)-6-propyl-5,6,7,8-tetrahydropyrido[4,3-d]pyrimidine dihydrochloride ¼ hydrate, 6-allyl-2-amino-4-(4-chlorophenyl) -5,6,7,8-tetrahydropyrido[4,3-d]pyrimidine dihydrochloride, 6-allyl-2-amino-4-(4-fluorophenyl) -5,6,7,8-tetrahydropyrido[4,3-d]pyrimidine dihydrochloride, 2-amino-4-(4-chlorophenyl)-6-methyl -5,6,7,8-tetrahydropyrido[4,3-d]pyrimidine ¼ hydrate, 6-acetyl-2-amino-4-phenyl-5,6,7,8-tetrahydropyrido[4,3-d]pyrimidine monohydrate, 2-amino-6-(2-diethylaminoethyl)-4-(4-fluorophenyl)-5,6,7,8tetrahydropyrido-[4,3-d]pyrimidine trihydrochloride and 2-amino-4-(4-fluorophenyl)-5,6,7,8-tetrahydro-6-(3-dimethylaminopropyl)-pyrido[4,3-d]pyrimidine trihydrochloride.

8. The compound of claim 1 wherein said compound is 6-acetyl-5,6,7,8-tetrahydro-4-(4-methylphenyl)-2-dipropylaminopyrido[4,3-d]pyrimidine monohydrate.

9. A pharmaceutical composition useful in treating gastrointestinal diseases comprising as an active ingredient an effective amount of the compound of claim 1, and a suitable pharmaceutical carrier.

10. A pharmaceutical composition useful in treating gastrointestinal diseases comprising as an active ingredient an effective amount of the compound of claim 2, and a suitable pharmaceutical carrier.

11. A pharmaceutical composition useful in treating gastrointestinal diseases comprising as an active ingredient an effective amount of the compound of claim 3, and a suitable pharmaceutical carrier.

12. A pharmaceutical composition useful in treating gastrointestinal diseases comprising as an active ingredient an effective amount of the compound of claim 4, and a suitable pharmaceutical carrier.

13. A pharmaceutical composition useful in treating gastrointestinal diseases comprising as an active ingredient an effective amount of the compound of claim 5, and a suitable pharmaceutical carrier.

14. A pharmaceutical composition useful in treating gastrointestinal diseases comprising as an active ingredient an effective amount of the compound of claim 6, and a suitable pharmaceutical carrier.

15. A pharmaceutical composition useful in treating gastrointestinal diseases comprising as an active ingredient an effective amount of the compound of claim 7, and a suitable pharmaceutical carrier.

16. A pharmaceutical composition useful in treating gastrointestinal diseases comprising as an active ingredient an effective amount of the compound of claim 8, and a suitable pharmaceutical carrier.

17. A method of treating gastrointestinal diseases in mammals by administering an effective amount of a compound of claim 1.

18. A method of treating gastrointestinal diseases in mammals by administering an effective amount of a compound of claim 2.

19. A method of treating gastrointestinal diseases in mammals by administering an effective amount of a compound of claim 3.

20. A method of treating gastrointestinal diseases in mammals by administering an effective amount of a compound of claim 4.

21. A method of treating gastrointestinal diseases in mammals by administering an effective amount of a compound of claim 5.

22. A method of treating gastrointestinal diseases in mammals by administering an effective amount of a compound of claim 6.

23. A method of treating gastrointestinal diseases in mammals by administering an effective amount of a compound of claim 7.

24. A method of treating gastrointestinal diseases in mammals by administering an effective amount of a compound of claim 8.

* * * * *